(12) United States Patent
Nielsen et al.

(10) Patent No.: US 9,181,296 B2
(45) Date of Patent: Nov. 10, 2015

(54) STABILIZED LIQUID ENZYME COMPOSITIONS

(75) Inventors: Lone Kierstein Nielsen, Kgs. Lyngby (DK); Lise Munch Mikkelsen, Roedovre (DK); Esben Peter Friis, Herlev (DK); Juergen Carsten Franz Knoetzel, Copenhagen Oe (DK); Ole Simonsen, Soeborg (DK); Lotte Rugholm Soerensen, Ballerup (DK)

(73) Assignee: NOVOZYMES A/S, Bagsvaerd (DK)

( * ) Notice: Subject to any disclaimer, the term of this patent is extended or adjusted under 35 U.S.C. 154(b) by 1302 days.

(21) Appl. No.: 12/933,895

(22) PCT Filed: Mar. 26, 2009

(86) PCT No.: PCT/EP2009/053580
§ 371 (c)(1),
(2), (4) Date: Sep. 22, 2010

(87) PCT Pub. No.: WO2009/118375
PCT Pub. Date: Oct. 1, 2009

(65) Prior Publication Data
US 2011/0039752 A1    Feb. 17, 2011

Related U.S. Application Data

(60) Provisional application No. 61/039,981, filed on Mar. 27, 2008.

(30) Foreign Application Priority Data

Mar. 26, 2008 (EP) .................................... 08153299

(51) Int. Cl.

| | | |
|---|---|---|
| C07K 5/08 | (2006.01) |
| C07K 5/10 | (2006.01) |
| C07K 2/00 | (2006.01) |
| C07K 5/083 | (2006.01) |
| C07K 5/09 | (2006.01) |
| C07K 5/103 | (2006.01) |
| C07K 5/107 | (2006.01) |
| C07K 5/117 | (2006.01) |
| C11D 3/386 | (2006.01) |
| C12N 9/54 | (2006.01) |
| C12N 9/96 | (2006.01) |

(52) U.S. Cl.
CPC .................. *C07K 5/0808* (2013.01); *C07K 2/00* (2013.01); *C07K 5/0806* (2013.01); *C07K 5/0817* (2013.01); *C07K 5/101* (2013.01); *C07K 5/1016* (2013.01); *C07K 5/1024* (2013.01); *C11D 3/38663* (2013.01); *C12N 9/54* (2013.01); *C12N 9/96* (2013.01)

(58) Field of Classification Search
None
See application file for complete search history.

(56) References Cited

U.S. PATENT DOCUMENTS

| | | |
|---|---|---|
| 4,568,476 A | 2/1986 | Kielman |
| 5,674,833 A | 10/1997 | Mikkelsen |
| 5,861,366 A | 1/1999 | Ihns |
| 6,165,966 A | 12/2000 | McIver et al. |
| 2002/0128444 A1 * | 9/2002 | Gingras et al. ................. 530/350 |
| 2003/0157088 A1 | 8/2003 | Elliott et al. |
| 2011/0212877 A1 | 9/2011 | Nielsen |

FOREIGN PATENT DOCUMENTS

| | | | |
|---|---|---|---|
| EP | 0 583 534 A * | 2/1994 | ............... C08K 5/08 |
| EP | 0583534 | 2/1994 | |
| EP | 0979864 | 2/2000 | |
| EP | 1953216 | 8/2008 | |
| JP | 10-66571 | 10/1998 | |
| WO | WO 92/03529 | 3/1992 | |
| WO | WO 94/04651 | 3/1994 | |
| WO | 94/29428 A1 | 12/1994 | |
| WO | WO 95/25791 | 9/1995 | |
| WO | WO 96/41638 | 12/1996 | |
| WO | 98/13461 A1 | 4/1998 | |
| WO | WO 98/13458 | 4/1998 | |
| WO | WO 98/13459 | 4/1998 | |
| WO | WO 98/13460 | * 4/1998 | ............... C07K 5/08 |
| WO | WO 98/13462 | 4/1998 | |
| WO | WO 98/54285 | 12/1998 | |
| WO | 99/20771 A2 | 4/1999 | |
| WO | WO 99/20726 | 4/1999 | |
| WO | WO 03/083030 | 10/2003 | |
| WO | WO 2005/105826 | 11/2005 | |
| WO | WO 2007/141736 | 12/2007 | |
| WO | WO 2007/145963 | 12/2007 | |
| WO | WO 2007/145964 | 12/2007 | |
| WO | WO 2009/102854 | 8/2009 | |
| WO | WO 2009/121890 | 10/2009 | |

OTHER PUBLICATIONS

Wikipedia "File:Phe Tyr.png" http://en.wikipedia.org/wiki/File:Phe_Tyr.png (downloaded May 15, 2014).*
Organic Chemistry Portal ("Protecting Groups" https://web.archive.org/web/20070429055422/http://www.organic-chemistry.org/protectivegroups/ (Apr. 29, 2007) downloaded May 15, 2014).*
Database Chemical Abstracts, XPOO2491496 (Dec. 2007).
Hajji et al., "Purification and characterization of an alkaline serine-protease produced by a new isolated *Aspergillus clavatus* ES1", Process Biochemistry, vol. 42, No. 5, pp. 791-797 (2007).
Search report issued in corresponding International Application No. PCT/EP2009/053580 dated Jan. 2010.
Broadbridge et al, 1998, Chem Commun, 1449-1450.

* cited by examiner

*Primary Examiner* — Karlheinz R Skowronek
*Assistant Examiner* — Mindy Newman
(74) *Attorney, Agent, or Firm* — Elias Lambiris; Kelly Reynolds

(57) ABSTRACT

Peptide aldehydes or ketone derivatives are particularly efficient for stabilizing subtilisin-type proteases in aqueous compositions such as liquid detergents, including peptide compounds with OH-substituted phenylalanine aldehyde as the C-terminal residue.

13 Claims, No Drawings

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Arg Ala Tyr His
1

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Gly Ala Tyr His
1

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Gly Ala Leu His
1

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Gly Ala Phe His
1
```

```
<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Gly Ala Val His
1

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Arg Val Tyr His
1

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Leu Val Tyr His
1

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Leu Gly Ala Tyr His
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Phe Gly Ala Tyr His
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Tyr Gly Ala Tyr His
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Phe Gly Val Tyr His
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Trp Leu Val Tyr His
1               5
```

STABILIZED LIQUID ENZYME COMPOSITIONS

CROSS-REFERENCE TO RELATED APPLICATIONS

This application is a 35 U.S.C. 371 national application of PCT/EP2009/053580 filed Mar. 26, 2009, which claims priority or the benefit under 35 U.S.C. 119 of European application no. 08153299.6 filed Mar. 26, 2008 and U.S. provisional application No. 61/039,981 filed Mar. 27, 2008, the contents of which are fully incorporated herein by reference.

FIELD OF THE INVENTION

The present invention relates to a liquid composition comprising a subtilisin and a peptide compound as a stabilizer for the subtilisin. It also relates to a peptide compound which is useful as a stabilizer for subtilisins.

BACKGROUND ART

Subtilisin-type proteases are well known in liquid aqueous detergents, particularly for use on laundry washing. A generally encountered problem in such liquid detergents is the degradation by the subtilisin of other enzymes in the composition and of the subtilisin itself. Consequently, the stability of the subtilisin and other enzymes in the liquid detergent composition is reduced, resulting in a liquid detergent with a reduced wash performance.

The prior art has dealt extensively with improving the storage stability of enzymes in liquid detergents, for example by adding various subtilisin inhibitors or stabilizers. Boric acid and boronic acids are known to reversibly inhibit proteolytic enzymes.

The use of peptide aldehydes for stabilizing certain proteases in liquid detergents is disclosed in WO 94/04651, WO 98/13458, WO 98/13459, WO 98/13460 and WO 98/13462. More specifically, WO94/04651 discloses the use of the peptide aldehydes Phe-Gly-Ala-PheH and Phe-Gly-Ala-LeuH for stabilizing subtilisin-type proteases. WO94/04651 also discloses Leu-Leu-TyrH as a suitable peptide aldehyde for stabilizing chymotrypsin-type proteases. Furthermore, WO94/04651 proposes methyl carbamate or methyl urea as an N-terminal protecting group of the peptide aldehydes. WO98/13460 discloses the use of peptide protease inhibitors, either peptide aldehydes or trifluoromethyl ketones, where the peptide chain contains 2-5 amino acids and the aldehyde/trifluromethyl ketone is derived from the amino acids alanine, valine, isoleucine, leucine, phenylglycine, phenylalanine or homophenylalanine and where the N-terminal protection group is preferably a sulphonamide or amidophoshate.

WO2007/141736, WO2007/145963 and WO2007/145964 disclose the use of a reversible peptide protease inhibitor to stabilize liquid detergent compositions. US2003/157088 describes compositions containing enzymes stabilized with inhibitors.

WO 96/41638 and WO 2005/105826 disclose peptide aldehydes and ketones.

SUMMARY OF THE INVENTION

The inventors have surprisingly found that certain peptide aldehydes or ketone derivatives are particularly efficient for stabilizing subtilisin-type proteases in aqueous compositions such as liquid detergents, including peptide compounds with OH-substituted phenylalanine as the C-terminal residue.

Accordingly, the invention provides a liquid composition comprising a subtilisin and a peptide compound of the formula $B_2$—$B_1$—$B_0$—R wherein:

R is hydrogen, $CH_3$, $CX_3$, $CHX_2$, or $CH_2X$, wherein X is a halogen atom; and $B_1$ is a single amino acid residue.

$B_0$ may be a phenylalanine residue with an OH substituent at the p-position and/or at a m-position; and $B_2$ may consist of one or more amino acid residues, $B_2$ optionally comprising an N-terminal protection group. Alternatively, $B_0$ may be a single amino acid residue; and $B_2$ is a residue of Gly, Arg or Leu with an N-terminal protection group attached.

The invention further provides a peptide compound of the formula $B_2$—$B_1$—$B_0$—R wherein:

R is hydrogen, $CH_3$, $CX_3$, $CHX_2$, or $CH_2X$, wherein X is a halogen atom; and $B_1$ is a single amino acid residue.

$B_0$ may be a phenylalanine residue with an OH substituent at the p-position and/or at a m-position; and $B_2$ may consist of one or more amino acid residues with benzyloxycarbonyl as an N-terminal protection group, or $B_2$ may be a residue of Gly, Arg or Leu with an N-terminal protection group attached. Alternatively, $B_0$ may be a single amino acid residue, and $B_1$ may be a small amino acid residue, and $B_2$ may be a residue of Gly, Arg or Leu with an aromatic N-terminal protection group attached.

DETAILED DISCLOSURE OF THE INVENTION

Definitions

An "amino acid residue" indicates a group with a structure like —NH—CHR—CO— written with the N-terminal at the left and the C-terminal at the right.

Amino acid residues are abbreviated using standard one-letter or three-letter abbreviations, including the following abbreviations: alanine (A), phenylalanine (F), glycine (G), leucine (L), arginine (R), valine (V), tryptophan (W), tyrosine (Y). The abbreviation "Y-H" denotes tyrosinal, meaning that the C-terminal end of the tyrosine residue is converted from a carboxylic group to an aldehyde group. The tyrosinal may be prepared by known processes.

Amino Acids

Each amino acid residue in $B_1$ and $B_2$ may be a natural or non-naturally occurring alpha- or beta-amino acid containing the structure —NH—$(CH(R))_n$—C(=O)—, where n=1-2 (preferably 1) and R is selected from linear or branched and/or cyclized, substituted or unsubstituted structures from the following groups: $C_1$-$C_6$ alkyl; phenyl; $C_7$-$C_9$ alkylaryl; $C_4$-$C_8$ cycloalkyl. Both L- and D-forms of amino acids are included.

The amino acid may be an α-amino acid such as any of the naturally occurring amino acids, norvaline (Nva), norleucine (Nle), homo-phenylalanine (Hph) or phenyl-glycine (Pgl). The α-amino carbon atom may be in the D- or L-configuration.

Peptide Compound

An OH-substituted phenylalanine such as tyrosine is a relatively hydrophilic amino acid, and its presence in a peptide will in general increase the solubility of the peptide compared to more hydrophobic amino acids like phenylalanine, leucine, alanine, cysteine, isoleucine, methionine and valine, which all have a positive hydropathy index compared to the negative hydropathy index of tyrosine (Kyte & Doolittle (1982), J. Mol. Biol. 157 (1), pp 105-132) (the larger hydropathy index is, the more hydrophibic amino acid).

The peptide compound may have the formula:

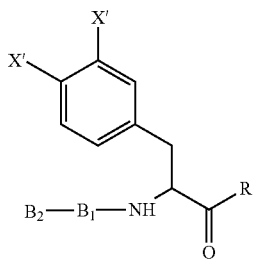

wherein R is hydrogen, $CH_3$, $CX_3$, $CHX_2$, or $CH_2X$, wherein X is a halogen atom; X' is OH or H, at least one X' being OH; $B_1$ is a single amino acid residue; and $B_2$ is one or more amino acid residues, $B_2$ optionally comprising an N-terminal protection group.

Thus, $B_0$ (the amino acid residue at the C-terminal) may be a residue of tyrosine (p-tyrosine), m-tyrosine or 3,4-dihydroxyphenylalanine. With a tyrosine residue, the peptide compound has the following formula:

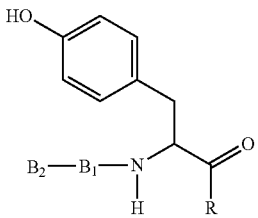

In one particular aspect of the invention, the peptide compound comprises only 3 amino acid residues including the C-terminal residue. In this aspect of the invention, the synthesis will be more cost-effective and the compounds have proven to be highly efficient inhibitors of enzyme activity. Preferably, the peptide compounds having only three amino acid residues are protected by an N-terminal protection group. Accordingly, in this aspect the invention relates to compounds wherein $B_2$ is a single amino acid residue comprising an N-terminal protection group.

In a preferred aspect of the invention, the peptide compound is an aldehyde comprising only 3 amino acid residues, where $B_2$ is selected among arginine, glycine and leucine comprising an N-terminal protection group. Where the peptide compound is an aldehyde comprising only 3 amino acid residues, $B_2$ is preferably selected among arginine and glycine comprising an N-terminal protection group.

In another aspect of the invention, the peptide compound comprises at least four amino acid residues. Preferably, the peptide compounds having at least four amino acid residues are protected by an N-terminal protection group. Accordingly, in this aspect the invention relates to compounds wherein $B_2$ is at least two amino acid residues comprising an N-terminal protection group.

In a preferred aspect, where the peptide compound comprises at least four amino acid residues, $B_2$ comprises an N-terminal amino acid residue having a non-polar side chain. In a more particular embodiment, the second amino acid residue of $B_2$, counted from the attachment to $B_1$, has a non-polar side chain. In an even more particular embodiment the peptide compound comprises four amino acid residues where the N-terminal amino acid residue having a non-polar side chain is selected among glycine, leucine, phenylalanine, tyrosine and tryptophan. Preferably, the N-terminal amino acid residue further comprises an N-terminal protection group.

It is preferred that $B_1$ is a small amino acid residue. More preferably $B_1$ is alanine or valine. In this context, the following are considered to be small amino acids: alanine, cysteine, glycine, proline, serine, threonine, valine, norvaline, norleucine.

The peptide compound may be an aldehyde wherein R is hydrogen, $B_1$ is a single amino acid, preferably selected among small amino acids such as valine and alanine, $B_2$ comprises at least two amino acid residues and wherein at least one of said two amino acid residues is selected among phenylalanine, glycine and leucine, and wherein the second amino acid residue of $B_2$ has a non-polar side chain selected among phenylalanine, glycine, leucine, tyrosine and tryptophan. Preferably, $B_2$ comprises an acetyl (Ac) N-terminal protection group, providing, inter alia, the peptide aldehyde compounds Ac-FGAY-H (SEQ ID NO: 9), Ac-LGAY-H (SEQ ID NO: 8), Ac-YGAY-H (SEQ ID NO: 10), Ac-FGVY-H (SEQ ID NO: 11) and Ac-WLVY-H (SEQ ID NO: 12). Preferably, the compounds according to this aspect of the invention comprise less than 10 amino acid residues, such as 9, 8, 7, 6, 5 or most preferably 4 amino acid residues.

In another aspect, the peptide compound may be a tripeptide aldehyde wherein R is hydrogen, $B_1$ is a single amino acid selected among small amino acids, e.g. valine and alanine, $B_2$ comprises an amino acid residue selected among arginine, glycine and leucine. Preferably, $B_2$ comprises an N-terminal protection group selected among benzyloxycarbonyl (Z) and acetyl (Ac), providing, inter alia, the peptide aldehyde compounds Z-RAY-H (SEQ ID NO: 1), Z-GAY-H (SEQ ID NO: 2), Z-GAL-H (SEQ ID NO: 3), Z-GAF-H (SEQ ID NO: 4), Z-GAV-H (SEQ ID NO: 5), Z-RVY-H (SEQ ID NO: 6), Z-LVY-H (SEQ ID NO: 7) and Ac-GAY-H (SEQ ID NO: 2). Most preferred, according to this aspect, is the benzyloxycarbonyl (Z) N-terminal protection group.

In a preferred aspect, where the peptide compound comprises at least four amino acid residues, $B_2$ comprises an N-terminal amino acid residue having a non-polar side chain. In the context of the present invention, by "amino acids with non-polar side chain" is meant an amino acid or amino acid residue selected from the group comprising: phenylalanine, tyrosine, tryptophan, isoleucine, leucine, methionine, valine, alanine, proline, glycine, norvaline, or norleucine.

Particularly preferred peptide aldehydes of the present invention include Z-RAY-H (SEQ ID NO: 1), Ac-GAY-H (SEQ ID NO: 2), Z-GAY-H (SEQ ID NO: 2), Z-GAL-H (SEQ ID NO: 3), Z-GAF-H (SEQ ID NO: 4), Z-GAV-H (SEQ ID NO: 5), Z-RVY-H (SEQ ID NO: 6), Z-LVY-H (SEQ ID NO: 7), Ac-LGAY-H (SEQ ID NO: 8), Ac-FGAY-H (SEQ ID NO: 9), Ac-YGAY-H (SEQ ID NO: 10), Ac-FGVY-H (SEQ ID NO: 11) or Ac-WLVY-H (SEQ ID NO: 12), where Z is benzyloxycarbonyl and Ac is acetyl.

N-Terminal Protecting Group

The N-terminal protecting group may be any amino-terminal protecting group which can be employed in peptide synthesis. Gross and Meinhoffer, eds., The Peptides, Vol. 3; 3-88 (1981), Academic Press, New York 1981, discloses numerous suitable amine protecting groups and is incorporated herein by reference for that purpose.

Examples of suitable groups include formyl, acetyl, benzoyl, trifluoroacetyl, fluoromethoxy carbonyl, methoxysuccinyl, aromatic urethane protecting groups, such as, benzyloxycarbonyl; and aliphatic urethane protecting groups, such as t-butyloxycarbonyl or adamantyloxycarbonyl, p-methoxybenzyl carbonyl (MOZ), benzyl (Bn), p-methoxybenzyl (PMB) or p-methoxyphenyl (PMP).

Preferably, the N-terminal protection group of the present invention is selected among formyl, acetyl, benzoyl, aromatic or aliphatic urethanes, more preferably acetyl or benzyloxycarbonyl. Where the peptide compound comprises three amino acids, the N-terminal protection group is preferably an aromatic or aliphatic urethane or an aromatic N-terminal protection group, particularly benzyloxycarbonyl (Cbz), p-methoxybenzyl carbonyl (MOZ), benzyl (Bn), p-methoxybenzyl (PMB) or p-methoxyphenyl (PMP), more preferably benzyloxycarbonyl. Where the peptide compound comprises four or more amino acids, it is preferred that the N-terminal protection group is formyl, acetyl or benzoyl, more preferably acetyl.

Liquid Composition

In a preferred embodiment, the peptide compounds of the present invention are used for stabilizing or inhibiting subtilisins in liquid compositions, which may further comprise a surfactant and other enzymes.

In one aspect, the invention further relates to the use of a compound as defined above for stabilizing and/or inhibiting enzymes including a subtilisin-type protease. In a preferred aspect, the enzymes are stabilized and/or inhibited in liquid detergents. Addition of the peptide compound to the liquid detergent may increase the detergency.

The liquid composition may be an enzyme composition comprising a subtilisin and optionally a second enzyme. The second enzyme may be any commercially available enzyme, in particular an enzyme selected from the group consisting of proteases, amylases, lipases, cellulases, mannanases, oxidoreductases, lyases and any mixture thereof. Mixtures of enzymes from the same class (e.g. proteases) are also included. The enzyme composition may also include other stabilizers, e.g. a polyol such as glycerol or propylene glycol, e.g. in an amount of 25-75% by weight.

The amount of enzyme used in the liquid composition varies according to the type of enzyme(s) and the type of composition. In a composition such as a liquid detergent the amount of each enzyme will typically be 0.04-80 micro-M, in particular 0.2-30 micro-M, especially 0.4-20 micro-M (generally 1-2000 mg/l, in particular 5-750 mg/l, especially 10-500 mg/l) calculated as pure enzyme protein. In a composition such as an enzyme concentrate the amount of each enzyme will typically be 0.01-20 mM, in particular 0.04-10 mM, especially 0.1-5 mM (generally 0.3-500 g/l, in particular 1-300 g/l, especially 3-150 g/l) calculated as pure enzyme protein.

The enzymes are normally incorporated into detergent compositions at levels sufficient to provide an in-wash effect, which will be known to the skilled person in the art. Normally this would be in the range from 0.0001% (w/w) to 5% (w/w). Typical amounts are in the range from 0.01% to 1% by weight of the liquid detergent composition. The molar ratio of enzyme stabilizer or inhibitor according to the invention to protease is at least 1:1 or 1.5:1, and it is less than 1000:1, more preferred less than 500:1, even more preferred from 100:1 to 2:1 or from 20:1 to 2:1, or most preferred, the molar ratio is from 10:1 to 3:1.

In one particular aspect, the invention relates to a composition comprising from 1 to 95% weight % of detersive surfactant(s), from 0.0001 to 5% by weight of a subtilisin, and from 0.00001 to 1% weight % of a peptide inhibitor as defined above. In a more particular embodiment, the invention relates to a composition comprising from 2 to 60% by weight of detersive surfactant(s), from 0.0005 to 1% by weight of a subtilisin, and from 0.00005 to 0.2% by weight of a peptide inhibitor as defined above. In an even more particular embodiment, the invention relates to a composition comprising from 3 to 50% by weight of detersive surfactant(s), from 0.001 to 0.5% by weight of a subtilisin, and from 0.0001 to 0.1% by weight of a peptide inhibitor as defined above.

Subtilisin

The subtilisin may be of animal, vegetable or microbial origin, including chemically or genetically modified mutants. It may be a serine protease, preferably an alkaline microbial protease. Examples are subtilisin-type proteases from the 1-S group defined by Siezen et al. (Protein Engineering, 1991, vol. 4 NO: 7 pp. 719-737) Examples of subtilisins are those derived from *Bacillus*, e.g., subtilisin Novo, subtilisin Carlsberg, subtilisin BPN', subtilisin 309, subtilisin 147 and subtilisin 168 (described in WO 89/06279). Examples are described in WO 1998/020115, WO 01/44452, WO 01/58275, WO 01/58276, WO 2003/006602, and WO 2004/099401.

Examples of commercially available proteases (peptidases) include Kannase™, Everlase™, Esperase™, Alcalase™, Neutrase™, Durazym™, Savinase™, Ovozyme™, Liquanase™, Polarzyme™, Pyrase™, Pancreatic Trypsin NOVO (PTN), Bio-Feed™ Pro and Clear-Lens™ Pro (all available from Novozymes NS, Bagsvaerd, Denmark). Other commercially available proteases include Ronozyme™ Pro, Maxatase™, Maxacal™, Maxapem™, Opticlean™, Properase™, Purafect™, Purafect Ox™ and Purafact Prime™ (available from Genencor International Inc., Gist-Brocades, BASF, or DSM Nutritional Products).

Second Enzyme

In addition to a subtilisin, the liquid composition may comprise a second enzyme selected from the group consisting of amylases, lipases, cellulases, mannanases, oxidoreductases and lyases; particularly preferred is a liquid composition in which the second enzyme is a lipase.

Suitable amylases (alpha and/or beta) include those of bacterial or fungal origin. Chemically or genetically modified mutants are included. Amylases include for example an alpha-amylase from *B. licheniformis*, described in GB 1,296, 839. Commercially available amylases are Duramyl™, Termamyl™, Stainzyme™, Stainzyme Plus™, Termamyl Ultra™, Fungamyl™ and BAN™ (available from Novozymes NS) and Rapidase™, Maxamyl P™, Purastar and Purastar OxAm (available from Gist-Brocades and Genencor Inc.).

Suitable cellulases may be of bacterial or fungal origin. Chemically or genetically modified mutants are included. It may be a fungal cellulase from *Humicola insolens* (U.S. Pat. No. 4,435,307) or from *Trichoderma*, e.g. *T. reesei* or *T. viride*. Examples of cellulases are described in EP 0 495 257. Commercially available cellulases include Carezyme™, Celluzyme™, Celluclean™, Celluclast™, and Endolase™ (available from Novozymes), Puradax, Puradax HA, and Puradax EG (available from Genencor).

Suitable oxidoreductases include a peroxidase or an oxidase such as a laccase. Chemically or genetically modified mutants are included. The peroxidase may be of plant, bacterial or fungal origin. Examples are peroxidases derived from a strain of *Coprinus*, e.g., *C. cinerius* or *C. macrorhizus*, or from a strain of *Bacillus*, e.g., *B. pumilus*, particularly peroxidase according to WO 91/05858. Suitable laccases herein include those of bacterial or fungal origin. Examples are laccases from *Trametes*, e.g., *T. villosa* or *T. versicolor*, or from a strain of *Coprinus*, e.g., *C. cinereus*, or from a strain of *Myceliophthora*, e.g., *M. thermophila*.

Suitable lipolytic enzymes include a lipase or cutinase of bacterial or fungal origin. Chemically or genetically modified mutants are included. Examples include a lipase from *Thermomyces lanuginosus* (*Humicola lanuginosa*) described in EP 258 068 and EP 305 216, a *Rhizomucor miehei* lipase, e.g., as described in EP 238 023, a *Candida* lipase, such as a *C. antarctica* lipase, e.g., the *C. antarctica* lipase A or B described in EP 214 761, a *Fusarium oxysporum* lipase (WO 98/26057), a *Pseudomonas* lipase such as a *P. pseudoalcaligenes* and *P. alcaligenes* lipase, e.g., as described in EP 218 272, a *P. cepacia* lipase, e.g., as described in EP 331 376, a *P. stutzeri* lipase, e.g., as disclosed in BP 1,372,034, a *P. fluorescens* lipase, a *Bacillus* lipase, e.g., a *B. subtilis* lipase (Dartois et al., (1993), Biochemica et Biophysica acta 1131, 253-260), a *B. stearothermophilus* lipase (JP 64/744992), *B. pumilus* lipase (WO 91/16422), *Penicillium camenbertii* lipase (Yamaguchi et al., (1991), Gene 103, 61-67), the *Geotrichum candidum* lipase (Shimada, Y. et al., (1989), J. Biochem. 106, 383-388), and various *Rhizopus* lipases such as a *R. delemar* lipase (Hass, M. J et al., (1991), Gene 109, 117-113), a *R. niveus* lipase (Kugimiya et al., (1992), Biosci. Biotech. Bio-chem. 56, 716-719) and a *R. oryzae* lipase. Additional examples are cutinase from *Pseudomonas mendocina* (WO 88/09367), cutinase from *Fusarium solani pisi* (WO 90/09446) and cutinase from *Humicola insolens* (WO 2001/092502). The lipolytic enzyme may be a lipase variant, e.g. described in WO 2000/060063.

Examples of commercially available lipases include Lipex™ Lipoprime™, Lipopan™ Lipopan F™ Lipopan Xtra™ Lipolase™, Lipolase™ Ultra, Lipozyme™, Palatase™, Resinase™ Noyozym™ 435 and Lecitase™ (all available from Novozymes NS). Other commercially available lipases include Lumafast™ (*Pseudomonas mendocina* lipase from Genencor International Inc.); Lipomax™ (*Ps. pseudoalcaligenes* lipase from Gist-Brocades/Genencor Int. Inc.); and *Bacillus* sp. lipase from Solvay enzymes. Further lipases are available from other suppliers such as Lipase P "Amano" (Amano Pharmaceutical Co. Ltd.).

Suitable mannanases include those of bacterial or fungal origin. Chemically or genetically modified mutants are included. Examples of commercially available mannanases include Mannaway™ (product of Novozymes) and MannaStar (product of Genencor).

Suitable lyases include those of bacterial or fungal origin. Chemically or genetically modified mutants are included. Examples of lyases include a pectate lyase and a pectin lyase. Examples of commercially available lyases are Pectawash™ and Pectaway™ (products of Novozymes).

The present invention is further described by the following examples which should not be construed as limiting the scope of the invention.

EXAMPLES

Example 1

Various peptide aldehydes were produced by a custom peptide synthesis company, all with a purity >80%. The peptide aldehydes were dissolved in DMSO to a concentration of 10 mg/ml before use.

A model liquid detergent was prepared for testing the various stabilizers:

Detergent Base:

| Component | % w/w |
|---|---|
| Sodium alkylethoxy sulphate (C9-15, 2EO) | 6.0 |
| Sodium dodecyl benzene sulphonate | 3.0 |
| Sodium toluene sulphonate | 3.0 |
| Oleic acid | 2.0 |
| Primary alcohol ethoxylate (C12-15, 7EO) | 3.0 |
| Primary alcohol ethoxylate (C12-15, 3EO) | 2.5 |
| Ethanol | 0.5 |
| Monopropylene glycol | 2.0 |
| Tri-sodium citrate 2H$_2$O | 4.0 |
| Triethanolamine | 0.4 |
| De-ionized water | Ad 100% |
| pH adjusted to 8.5 with NaOH | |

A reference detergent with enzymes was prepared:

Detergent A:

| Component | % w/w |
|---|---|
| Detergent base | 99.0 |
| Protease (Savinase 16.0 LEX) | 0.5 |
| Lipase (Lipex 100L) | 0.5 |

Further the following detergents with stabilizers from the invention were prepared, all samples normalized to 100 g of detergent:

| Detergent ID | Detergent A | Stabilizer (from a 10 mg/ml solution) | Molar surplus of inhibitor relative to protease |
|---|---|---|---|
| B1 | 100 g | 1.3 mg Z-RAY-H (SEQ ID NO: 1) | 3 |
| B2 | 100 g | 2.2 mg Z-RAY-H (SEQ ID NO: 1) | 5 |
| B3 | 100 g | 4.4 mg Z-RAY-H (SEQ ID NO: 1) | 10 |
| C1 | 100 g | 2.8 mg Ac-GAY-H (SEQ ID NO: 2) | 10 |
| C2 | 100 g | 7.0 mg Ac-GAY-H (SEQ ID NO: 2) | 25 |
| D1 | 100 g | 1.8 mg Z-GAY-H (SEQ ID NO: 2) | 5 |
| D2 | 100 g | 3.6 mg Z-GAY-H (SEQ ID NO: 2) | 10 |
| E1 | 100 g | 1.4 mg Z-RVY-H (SEQ ID NO: 6) | 3 |
| E2 | 100 g | 2.3 mg Z-RVY-H (SEQ ID NO: 6) | 5 |
| E3 | 100 g | 4.6 mg Z-RVY-H (SEQ ID NO: 6) | 10 |
| F1 | 100 g | 1.3 mg Z-LVY-H (SEQ ID NO: 7) | 3 |
| F2 | 100 g | 2.1 mg Z-LVY-H (SEQ ID NO: 7) | 5 |
| F3 | 100 g | 4.3 mg Z-LVY-H (SEQ ID NO: 7) | 10 |
| G1 | 100 g | 1.1 mg Ac-LGAY-H (SEQ ID NO: 8) | 3 |
| G2 | 100 g | 1.9 mg Ac-LGAY-H (SEQ ID NO: 8) | 5 |
| G3 | 100 g | 3.7 mg Ac-LGAY-H (SEQ ID NO: 8) | 10 |
| H1 | 100 g | 0.6 mg Ac-FGAY-H (SEQ ID NO: 9) | 1.5 |
| H2 | 100 g | 1.2 mg Ac-FGAY-H (SEQ ID NO: 9) | 3 |
| H3 | 100 g | 2 mg Ac-FGAY-H (SEQ ID NO: 19) | 5 |
| H4 | 100 g | 4 mg Ac-FGAY-H (SEQ ID NO: 9) | 10 |
| H5 | 100 g | 10 mg Ac-FGAY-H (SEQ ID NO: 9) | 25 |
| I1 | 100 g | 1.2 mg Ac-YGAY-H (SEQ ID NO: 10) | 3 |
| I2 | 100 g | 2.1 mg Ac-YGAY-H (SEQ ID NO: 10) | 5 |
| I3 | 100 g | 4.2 mg Ac-YGAY-H (SEQ ID NO: 10) | 10 |
| J1 | 100 g | 1.3 mg Ac-FGVY-H (SEQ ID NO: 11) | 3 |
| J2 | 100 g | 2.1 mg Ac-FGVY-H (SEQ ID NO: 11) | 5 |
| J3 | 100 g | 4.3 mg Ac-FGVY-H (SEQ ID NO: 11) | 10 |
| K1 | 100 g | 1.5 mg Ac-WLVY-H (SEQ ID NO: 12) | 3 |
| K2 | 100 g | 2.5 mg Ac-WLVY-H (SEQ ID NO: 12) | 5 |
| K3 | 100 g | 5.1 mg Ac-WLVY-H (SEQ ID NO: 12) | 10 |

The detergents were placed in closed glasses at 35° C. and 40° C. Residual activity of lipase and protease was measured (by comparison to a reference stored at −18° C.) at different times, using standard enzyme analytical methods (protease measured by hydrolysis of N,N-dimethylcasein at 40° C., pH 8.3 and lipase measured by hydrolysis of p-nitrophenyl valerate at 40° C., pH 7.7). In the table below, 3× denotes 3 molar surplus of the inhibitor compared to the protease etc.

| Detergent | Residual protease activity 1 week 40° C. | Residual Lipase activity 1 week 35° C. |
|---|---|---|
| A (reference) | 11% | 3% |
| B1 (Z-RAY-H, 3x) (SEQ ID NO: 1) | 49% | 12% |
| B2 (Z-RAY-H, 5x) (SEQ ID NO: 1) | 69% | 37% |
| B3 (Z-RAY-H, 10x) (SEQ ID NO: 1) | 79% | 63% |
| C1 (Ac-GAY-H, 10x) (SEQ ID NO: 2) | 59% | |
| C2 (Ac-GAY-H, 25x) (SEQ ID NO: 2) | 73% | 62% |
| D1 (Z-GAY-H, 5x) (SEQ ID NO: 2) | 55% | 22% |
| D2 (Z-GAY-H, 10x) (SEQ ID NO: 2) | 77% | 49% |
| E1 (Z-RVY-H, 3x) (SEQ ID NO: 6) | 54% | 21% |
| E2 (Z-RVY-H, 5x) (SEQ ID NO: 6) | 67% | 36% |
| E3 (Z-RVY-H, 10x) (SEQ ID NO: 6) | 80% | 61% |
| F1 (Z-LVY-H, 3x) (SEQ ID NO: 7) | 32% | 7% |
| F2 (Z-LVY-H, 5x) (SEQ ID NO: 7) | 43% | 15% |
| F3 (Z-LVY-H, 10x) (SEQ ID NO: 7) | 59% | 33% |
| G1 (Ac-LGAY-H, 3x) (SEQ ID NO: 8) | 62% | 33% |
| G2 (Ac-LGAY-H, 5x) (SEQ ID NO: 8) | 82% | 56% |
| G3 (Ac-LGAY-H, 10x) (SEQ ID NO: 8) | 90% | 66% |
| H1 (Ac-FGAY-H, 1.5x) (SEQ ID NO: 9) | 24% | 4% |
| H2 (Ac-FGAY-H, 3x) (SEQ ID NO: 9) | 42% | 12% |
| H3 (Ac-FGAY-H, 5x) (SEQ ID NO: 9) | 78% | 63% |
| H4 (Ac-FGAY-H, 10x) (SEQ ID NO: 9) | 91% | 72% |
| H5 (Ac-FGAY-H, 25x) (SEQ ID NO: 9) | 93% | 72% |
| I1 (Ac-YGAY-H, 3x) (SEQ ID NO: 10) | 53% | 14% |
| I2 (Ac-YGAY-H, 5x) (SEQ ID NO: 10) | 90% | 66% |
| I3 (Ac-YGAY-H, 10x) (SEQ ID NO: 10) | 88% | 75% |

-continued

| Detergent | Residual protease activity 1 week 40° C. | Residual Lipase activity 1 week 35° C. |
|---|---|---|
| J1 (Ac-FGVY-H, 3x) (SEQ ID NO: 11) | 62% | 48% |
| J2 (Ac-FGVY-H, 5x) (SEQ ID NO: 11) | 82% | 66% |
| J3 (Ac-FGVY-H, 10x) (SEQ ID NO: 11) | 96% | 70% |
| K1 (Ac-WLVY-H, 3x) (SEQ ID NO: 12) | 26% | 3% |
| K2 (Ac-WLVY-H, 5x) (SEQ ID NO: 12) | 35% | 8% |
| K3 (Ac-WLVY-H, 10x) (SEQ ID NO: 12) | 53% | 18% |

The results demonstrate that tyrosinal peptide aldehydes are very efficient protease stabilizers.

Example 2

The following reference detergent with enzymes was prepared:
Detergent L:

| Component | % w/w |
|---|---|
| Detergent base from ex. 1 | 98.5 |
| Protease (Savinase 16.0 LEX) | 0.5 |
| Lipase (Lipex 100L) | 0.5 |
| Amylase (Stainzyme 12L) | 0.5 |

The following detergent with stabilizer according to the invention was prepared and normalized to 100 g of detergent:

| Detergent ID | Detergent L | Stabilizer (from a 10 mg/ml solution) | Molar surplus of inhibitor relative to protease |
|---|---|---|---|
| M | 100 g | 2 mg Ac-FGAY-H (SEQ ID NO: 9) | 5 |

The detergents were placed in closed glasses at 25° C. and 35° C. Residual activity of lipase, amylase and protease was measured (by comparison to a reference stored at −18° C.) at different times (w=weeks), using standard enzyme analytical methods (protease measured by hydrolysis of N,N-dimethyl-casein at 40° C., pH 8.3, lipase measured by hydrolysis of p-nitrophenyl valerate at 40° C., pH 7.7 and amylase measured by hydrolysis of 4,6-ethylidene-($G_7$) p-nitrophenyl-($G_1$)-α,D-maltoheptasoid at 37° C., pH 7.35)

| | % residual activity | | | | | |
|---|---|---|---|---|---|---|
| | Residual protease activity | | Residual lipase activity | | Residual amylase activity | |
| Detergent | 4w35° C. | 13w25° C. | 4w35° C. | 13w25° C. | 4w35° C. | 13w25° C. |
| L (reference) | 35% | 62% | 1% | 2% | 34% | 42% |
| M (Ac-FGAY-H, 5x) (SEQ ID NO: 9) | 91% | 100% | 16% | 71% | 70% | 88% |

It is seen that the tyrosinal peptide aldehyde significantly improves the storage stability of the protease, lipase and amylase in a liquid detergent.

Example 3

Peptide aldehydes Z-GAF-H, Z-GAL-H and Z-GAY-H were produced by peptide synthesis, all with a purity >80%. The peptide aldehydes were dissolved in DMSO to a concentration of 10 mg/ml before use.

The following detergent N with enzymes was prepared:

| Component | % w/w |
|---|---|
| Sodium alkylethoxy sulphate (C9-15, 2EO) | 20.0 |
| Sodium toluene sulphonate | 3.0 |
| Oleic acid | 4.0 |
| Primary alcohol ethoxylate (C12-15, 7EO) | 2.5 |
| Primary alcohol ethoxylate (C12-15, 3EO) | 2.0 |
| Ethanol | 2.1 |
| Sodium carbonate | 4.5 |
| Tri-sodium citrate 2H$_2$O | 5.0 |
| De-ionized water | Ad 99% |
| pH adjusted to 8.0 with NaOH | |
| Protease (Savinase 16.0 LEX) | 0.5 |
| Lipase (Lipex 100L) | 0.5 |

The following detergents with stabilizer according to the invention were prepared and normalized to 100 g of detergent:

| Detergent ID | Detergent N | Stabilizer (from a 10 mg/ml solution) | Molar surplus of inhibitor relative to protease |
| --- | --- | --- | --- |
| P (reference) | 100 g | none | 0 |
| Q1 | 100 g | 0.16 mg Z-GAL-H (SEQ ID NO: 3) | 0.5 |
| Q2 | 100 g | 0.31 mg Z-GAL-H (SEQ ID NO: 3) | 1.0 |
| Q3 | 100 g | 0.62 mg Z-GAL-H (SEQ ID NO: 3) | 2.0 |
| Q4 | 100 g | 1.6 mg Z-GAL-H (SEQ ID NO: 3) | 5.0 |
| R1 | 100 g | 0.17 mg Z-GAF-H (SEQ ID NO: 4) | 0.5 |
| R2 | 100 g | 0.34 mg Z-GAF-H (SEQ ID NO: 4) | 1.0 |
| R3 | 100 g | 0.68 mg Z-GAF-H (SEQ ID NO: 4) | 2.0 |
| R4 | 100 g | 1.7 mg Z-GAF-H (SEQ ID NO: 4) | 5.0 |
| S1 | 100 g | 0.18 mg Z-GAY-H (SEQ ID NO: 2) | 0.5 |
| S2 | 100 g | 0.35 mg Z-GAY-H (SEQ ID NO: 2) | 1.0 |
| S3 | 100 g | 0.71 mg Z-GAY-H (SEQ ID NO: 2) | 2.0 |
| S4 | 100 g | 1.8 mg Z-GAY-H (SEQ ID NO: 2) | 5.0 |

The detergents were placed in closed glasses at 40° C. Residual activity of protease was measured (by comparison to a reference stored at −18° C.) after 1 week, using standard enzyme analytical methods (protease measured by hydrolysis of N,N-dimethylcasein at 40° C., pH 8.3).

% residual protease activity after 1 week at 40° C.:

| Molar surplus of inhibitor relative to protease | Det N (reference) | Det N + Z-GAL-H | Det N + Z-GAF-H | Det N + Z-GAY-H |
| --- | --- | --- | --- | --- |
| 0 | 7% (P) | | | |
| 0.5 | | 12% (Q1) | 11% (R1) | 13% (S1) |
| 1 | | 17% (Q2) | 18% (R2) | 28% (S2) |
| 2 | | 31% (Q3) | 28% (R3) | 41% (S3) |
| 5 | | 42% (Q4) | 44% (R4) | 65% (S4) |

The results demonstrate that all three peptide aldehydes are efficient for stabilizing the protease. The tyrosinal peptide aldehyde Z-GAY-H (SEQ ID NO: 2) was found to be the most efficient as it requires only approximately half the molar surplus of inhibitor relative to protease to reach the same residual activities as the other peptide aldehydes.

---

The invention claimed is:

1. A liquid composition comprising a subtilisin and a peptide compound of the formula $B_2$—$B_1$—$B_0$—R wherein:
   R is hydrogen, $CH_3$, $CX_3$, $CHX_2$, or $CH_2X$, wherein X is a halogen atom;
   $B_0$ is a Tyr residue;
   $B_1$ is a single amino acid residue; and
   $B_2$ consists of one or more amino acid residues, optionally comprising an N-terminal protection group.

2. The liquid composition of claim 1, wherein $B_2$ consists of one or two amino acid residues comprising an N-terminal protection group.

3. A liquid composition comprising a subtilisin and a peptide compound of the formula $B_2$—$B_1$—$B_0$—R wherein:
   R is hydrogen, $CH_3$, $CX_3$, $CHX_2$, or $CH_2X$, wherein X is a halogen atom;
   $B_0$ is a Tyr residue;
   $B_1$ is a single amino acid residue; and
   $B_2$ is a residue of Gly, Arg or Leu with an N-terminal protection group attached.

4. The liquid composition of claim 1 wherein $B_1$ is a residue of Ala, Cys, Gly, Pro, Ser, Thr, Val, Nva or Nle.

5. The liquid composition of claim 1, wherein $B_2$ comprises an N-terminal protection group selected from formyl, acetyl, benzoyl, trifluoroacetyl, fluoromethoxy carbonyl, methoxysuccinyl, aromatic and aliphatic urethane protecting groups, benzyloxycarbonyl, t-butyloxycarbonyl, adamantyloxycarbonyl, p-methoxybenzyl carbonyl (MOZ), benzyl (Bn), p-methoxybenzyl (PMB) or p-methoxyphenyl (PMP).

6. A liquid composition comprising a subtilisin and a peptide compound, wherein the peptide compound is the peptide aldehyde Z-RAY-H (SEQ ID NO: 1), Ac-GAY-H (SEQ ID NO: 2), Z-GAY-H (SEQ ID NO: 2), Z-GAL-H (SEQ ID NO: 3), Z-GAF-H (SEQ ID NO: 4), Z-GAV-H (SEQ ID NO: 5), Z-RVY-H (SEQ ID NO: 6), Z-LVY-H (SEQ ID NO: 7), Ac-LGAY-H (SEQ ID NO: 8), Ac-FGAY-H (SEQ ID NO: 9), Ac-YGAY-H (SEQ ID NO: 10), Ac-FGVY-H (SEQ ID NO: 11) or Ac-WLVY-H (SEQ ID NO: 12), wherein Z is benzyloxycarbonyl and Ac is acetyl.

7. The liquid composition of claim 1 which is a liquid detergent composition further comprising a surfactant.

8. A peptide compound of the formula $B_2$—$B_1$—$B_0$—R wherein:
   R is hydrogen, $CH_3$, $CX_3$, $CHX_2$, or $CH_2X$, wherein X is a halogen atom;
   $B_0$ is a Tyr residue;
   $B_1$ is a single amino acid residue; and
   $B_2$ consists of one or more amino acid residues with benzyloxycarbonyl as an N-terminal protection group.

9. A peptide compound of the formula $B_2$—$B_1$—$B_0$—R wherein:
   R is hydrogen, $CH_3$, $CX_3$, $CHX_2$, or $CH_2X$, wherein X is a halogen atom;
   $B_0$ is a Tyr residue;
   $B_1$ is a single amino acid residue; and
   $B_2$ is a residue of Gly, Arg, or Leu with an N-terminal protection group attached.

10. The peptide compound of claim 8, wherein $B_2$ comprises an N-terminal protection group selected from formyl, acetyl, benzoyl, trifluoroacetyl, fluoromethoxy carbonyl, methoxysuccinyl, aromatic and aliphatic urethane protecting groups, benzyloxycarbonyl, t-butyloxycarbonyl, adamantyloxycarbonyl, p-methoxybenzyl carbonyl (MOZ), benzyl (Bn), p-methoxybenzyl (PMB) or p-methoxyphenyl (PMP).

11. A peptide compound of the formula $B_2$—$B_1$—$B_0$—R wherein:
   R is hydrogen, $CH_3$, $CX_3$, $CHX_2$, or $CH_2X$, wherein X is a halogen atom;
   $B_0$ is Tyr residue;
   $B_1$ is a small amino acid residue; and
   $B_2$ is a residue of Gly, Arg or Leu with an aromatic N-terminal protection group attached.

12. The peptide compound of claim 11 wherein the aromatic N-terminal protection group is benzyloxycarbonyl (Cbz), p-methoxybenzyl carbonyl (MOZ), benzyl (Bn), p-methoxybenzyl (PMB) or p-methoxyphenyl (PMP).

13. A peptide aldehyde of the formula Z-RAY-H (SEQ ID NO: 1), Ac-GAY-H (SEQ ID NO: 2), Z-GAY-H (SEQ ID NO: 2), Z-GAL-H (SEQ ID NO: 3), Z-GAF-H (SEQ ID NO: 4), Z-GAV-H (SEQ ID NO: 5), Z-RVY-H (SEQ ID NO: 6), Z-LVY-H (SEQ ID NO: 7), Ac-LGAY-H (SEQ ID NO: 8), Ac-FGAY-H (SEQ ID NO: 9), Ac-YGAY-H (SEQ ID NO: 10), Ac-FGVY-H (SEQ ID NO: 11) or Ac-WLVY-H (SEQ ID NO: 12), wherein Z is benzyloxycarbonyl and Ac is acetyl.

* * * * *